United States Patent
Berend et al.

(10) Patent No.: US 10,973,580 B2
(45) Date of Patent: Apr. 13, 2021

(54) METHOD AND SYSTEM FOR PLANNING AND PERFORMING ARTHROPLASTY PROCEDURES USING MOTION-CAPTURE DATA

(71) Applicant: Biomet Manufacturing, LLC, Warsaw, IN (US)

(72) Inventors: Michael E. Berend, Indianapolis, IN (US); Keith R. Berend, Columbus, OH (US); Adolph V. Lombardi, New Albany, OH (US); Kirk J Bailey, Rochester, IN (US); John White, Winona Lake, IN (US)

(73) Assignee: Biomet Manufacturing, LLC, Warsaw, IN (US)

( * ) Notice: Subject to any disclaimer, the term of this patent is extended or adjusted under 35 U.S.C. 154(b) by 443 days.

(21) Appl. No.: 15/081,370

(22) Filed: Mar. 25, 2016

(65) Prior Publication Data
US 2016/0278868 A1    Sep. 29, 2016

Related U.S. Application Data (60) Provisional application No. 62/138,452, filed on Mar. 26, 2015.

(51) Int. Cl.
*A61B 34/10* (2016.01)
*A61B 5/11* (2006.01)
(Continued)

(52) U.S. Cl.
CPC ............ *A61B 34/10* (2016.02); *A61B 5/1071* (2013.01); *A61B 5/1121* (2013.01);
(Continued)

(58) Field of Classification Search
CPC ..... A61B 34/10; A61B 5/1071; A61B 5/1121; A61B 5/4851
See application file for complete search history.

(56) References Cited

U.S. PATENT DOCUMENTS 7,840,256 B2    11/2010  Lakin et al.
8,167,823 B2     5/2012  Nycz et al.
(Continued)

FOREIGN PATENT DOCUMENTS

CN          1356671       7/2002
CN        101379530       3/2009
(Continued)

OTHER PUBLICATIONS

R. Hofstetter, M. Slomczykowski, M. Sati & L.-P. Nolte (1999) Fluoroscopy as an Imaging Means for Computer-Assisted Surgical Navigation, Computer Aided Surgery, 4:2, 65-76 (Year: 1999).*
(Continued)

*Primary Examiner* — Daniel L Cerioni
*Assistant Examiner* — Raymond P Dulman
(74) *Attorney, Agent, or Firm* — Schwegman Lundberg & Woessner, P.A.

(57) ABSTRACT

A method of preparing a surgical plan comprises video capturing a range of motion of an anatomic joint of a patient to obtain a range of motion video, registering the range of motion video to two-dimensional images of a skeleton of the patient, identifying potential impingement and stability issues in the anatomic joint based on the range of motion video, templating a prosthetic implant on two-dimensional images of the anatomic joint using the identified potential impingement and stability issues of the anatomic joint to obtain position and orientation data, and electronically saving the position and orientation data of the prosthetic implant for use with a surgical navigation system. A system (Continued)

for planning and performing a surgical procedure comprises a motion capture system, an x-ray system, an electronic modeling system, and a surgical navigation system.

8 Claims, 6 Drawing Sheets

(51) Int. Cl.
*A61B 5/107* (2006.01)
*A61B 5/00* (2006.01)
*G06F 3/01* (2006.01)
*A61F 2/46* (2006.01)
*A61F 2/30* (2006.01)
*A61B 34/20* (2016.01)
*A61B 90/00* (2016.01)
*A61B 90/50* (2016.01)
*A61B 34/00* (2016.01)

(52) U.S. Cl.
CPC .......... *A61B 5/1127* (2013.01); *A61B 5/4851* (2013.01); *A61F 2/4609* (2013.01); *G06F 3/011* (2013.01); *A61B 5/0035* (2013.01); *A61B 5/0077* (2013.01); *A61B 34/25* (2016.02); *A61B 2034/104* (2016.02); *A61B 2034/105* (2016.02); *A61B 2034/107* (2016.02); *A61B 2034/108* (2016.02); *A61B 2034/2048* (2016.02); *A61B 2034/2051* (2016.02); *A61B 2034/2055* (2016.02); *A61B 2034/2065* (2016.02); *A61B 2090/364* (2016.02); *A61B 2090/376* (2016.02); *A61B 2090/3937* (2016.02); *A61B 2090/3966* (2016.02); *A61B 2090/502* (2016.02); *A61B 2505/05* (2013.01); *A61F 2002/30952* (2013.01); *A61F 2002/4633* (2013.01)

(56) References Cited

U.S. PATENT DOCUMENTS

| | | | |
|---|---|---|---|
| 8,571,637 B2 | 10/2013 | Sheffer et al. | |
| 8,876,830 B2 | 11/2014 | Hodorek et al. | |
| 9,142,024 B2 | 9/2015 | Sullivan et al. | |
| 2002/0037092 A1 | 3/2002 | Craig et al. | |
| 2002/0082498 A1 | 6/2002 | Wendt et al. | |
| 2002/0087274 A1 | 7/2002 | Alexander et al. | |
| 2004/0116804 A1* | 6/2004 | Mostafavi | A61B 5/1128 600/428 |
| 2005/0281465 A1 | 12/2005 | Marquart et al. | |
| 2007/0287900 A1* | 12/2007 | Breen | A61B 5/1116 600/407 |
| 2007/0288030 A1* | 12/2007 | Metzger | A61B 17/154 606/87 |
| 2008/0257363 A1* | 10/2008 | Schoenefeld | A61F 2/30942 128/897 |
| 2008/0262812 A1* | 10/2008 | Arata | G06F 19/00 703/11 |
| 2008/0269596 A1 | 10/2008 | Revie et al. | |
| 2008/0294258 A1* | 11/2008 | Revie | A61B 5/7246 623/16.11 |
| 2010/0076563 A1 | 3/2010 | Otto et al. | |
| 2010/0100193 A1* | 4/2010 | White | A61F 2/46 623/22.43 |
| 2010/0164862 A1 | 7/2010 | Sullivan et al. | |
| 2010/0198067 A1* | 8/2010 | Mahfouz | G16H 50/50 600/443 |
| 2010/0249657 A1 | 9/2010 | Nycz et al. | |
| 2010/0298894 A1* | 11/2010 | Bojarski | A61B 17/1764 606/86 R |
| 2011/0218543 A1* | 9/2011 | van der Walt | A61B 17/56 606/88 |
| 2011/0257653 A1 | 10/2011 | Hughes et al. | |
| 2012/0008848 A1* | 1/2012 | Beck | G06T 7/60 382/132 |
| 2013/0185310 A1 | 7/2013 | De Guise et al. | |
| 2013/0307955 A1* | 11/2013 | Deitz | G06F 19/00 348/77 |
| 2014/0189508 A1* | 7/2014 | Granchi | A61B 34/25 715/705 |
| 2015/0142372 A1* | 5/2015 | Singh | A61B 5/4851 702/150 |
| 2015/0254859 A1* | 9/2015 | Parikh | G06T 7/74 382/103 |

FOREIGN PATENT DOCUMENTS

| | | |
|---|---|---|
| CN | 102341767 | 2/2012 |
| CN | 102933163 A | 2/2013 |
| CN | 103211655 A | 7/2013 |
| CN | 107995855 A | 5/2018 |
| JP | 2010524562 A | 7/2010 |
| WO | 2006099589 | 9/2006 |
| WO | WO-2016154554 A1 | 9/2016 |

OTHER PUBLICATIONS

Bauman and Chang, High-speed X-ray video demonstrates significant skin movement errors with standard optical kinematics during rat locomotion, 2010, Journal of Neuroscience Methods, 186, p. 18-24. (Year: 2010).*
"Acumen™ Surgical Navigation System, Surgical Navigation Applications", Biomet Brochure, (2003), 2 pgs.
"Acumen™ Surgical Navigation System, Understanding Surgical Navigation", Biomet Brochure, (2003), 2 pgs.
Stiehl, James B., et al., "Navigation and Robotics in Total Joint and Spine Surgery", Chapter 3: C-Arm-Based Navigation, Springer-Verlag, (2004), 7 pgs.
"International Application Serial No. PCT/US2016/024256, International Preliminary Report on Patentability dated Oct. 5, 2017", 8 pgs.
"European Application Serial No. 16714715.6, Response filed May 24, 2018 to Office Action dated Nov. 14, 2017", 64 pgs.
"International Application Serial No. PCT/US2016/024256, International Search Report dated Jun. 13, 2016", 5 pgs.
"International Application Serial No. PCT/US2016/024256, Written Opinion dated Jun. 13, 2016", 6 pgs.
"Chinese Application Serial No. 201680028765.3, Office Action dated Mar. 17, 2020", (W/ English Translation), 17 pgs.
"European Application Serial No. 16714715.6, Communication Pursuant to Article 94(3) EPC dated Feb. 18, 2020", 4 pgs.
"Japanese Application Serial No. 2017-550114, Notification of Reasons for Rejection dated Feb. 4, 2020", (W/ English Translation), 9 pgs.
"Japanese Application Serial No. 2017-550114, Response filed Apr. 14, 2020 to Notification of Reasons for Rejection dated Feb. 4, 2020", (W/ English claims), 13 pgs.
Conn, K. S., et al., "A simple guide to determine the magnification of radiographs and to improve the accuracy of preoperative templating", The Journal of Bone and Joint Surgery; vol. 84-B, No. 2, (Mar. 2002), p. 269-272.
"Japanese Application Serial No. 2017-550114, Response filed Apr. 14, 2020 to Notification of Reason for Rejection dated Feb. 4, 2020", (W/ English claims), 13 pgs.
"Chinese Application Serial No. 201680028765.3, Response filed Jul. 31, 2020 to Office Action dated Mar. 17, 2020", w/ English claims, 16 pgs.
"European Application Serial No. 16714715.6, Response filed Jun. 29, 2020 to Communication Pursuant to Article 94(3) EPC dated Feb. 18, 2020", 16 pgs.
"Japanese Application Serial No. 2017-550114, Examiners Decision of Final Refusal dated Oct. 6, 2020", with English translation, 8 pages.

(56) References Cited

OTHER PUBLICATIONS

"Chinese Application Serial No. 201680028765.3, Office Action dated Nov. 11, 2020", with English translation, 18 pages.

* cited by examiner

METHOD AND SYSTEM FOR PLANNING AND PERFORMING ARTHROPLASTY PROCEDURES USING MOTION-CAPTURE DATA

CLAIM OF PRIORITY

This patent application claims the benefit of priority of Berend et al., U.S. Provisional Patent Application Ser. No. 62/138,452, entitled "PATIENT-SPECIFIC HIP PLANNING AND POSITIONING ALGORITHM," filed on Mar. 26, 2015, which is hereby incorporated by reference herein in its entirety.

TECHNICAL FIELD

This document pertains generally, but not by way of limitation, to systems and methods for planning and performing arthroplasty procedures. More particularly, this disclosure relates to, but not by way of limitation, pre-operative planning techniques to facilitate prosthetic fit and intra-operative alignment features to facilitate prosthetic placement and implantation.

BACKGROUND

Surgical navigation systems, also known as computer assisted surgery and image guided surgery, aid surgeons in locating patient anatomical structures, guiding surgical instruments, and implanting medical devices with a high degree of accuracy. A surgical navigation system typically includes a computer, a tracking system and patient anatomical information. The patient anatomical information can be obtained by using an imaging mode such as fluoroscopy, computer tomography (CT) or by simply defining the location of patient anatomy with the surgical navigation system. Surgical navigation systems can be used for a wide variety of surgeries to improve patient outcomes.

To successfully implant a medical device, surgical navigation systems often employ various forms of computing technology, as well as utilize intelligent instruments, digital touch devices, and advanced 3-D visualization software programs. All of these components enable surgeons to perform a wide variety of standard and minimally invasive surgical procedures and techniques. Moreover, these systems allow surgeons to more accurately plan, track and navigate the placement of instruments and implants relative to a patient's body, as well as conduct pre-operative and intra-operative body imaging.

To accomplish the accurate planning, tracking and navigation of surgical instruments, tools and/or medical devices during a surgical procedure utilizing surgical navigation, surgeons often use "tracking arrays" that are coupled to the surgical components. These tracking arrays allow the surgeons to track the physical location of these surgical components, as well as the patient's anatomy during the surgery. By knowing the physical location of the tracking array, software associated with the tracking system can accurately calculate the position of the tracked component relative to a surgical plan image.

Surgical navigation systems, however, can be limited by the information they are provided with during the pre-operative planning stage. For example, a surgical navigation system can only guide a prosthetic implant into proper alignment as accurately as the surgical plan was pre-operatively outlined. Thus, if the surgical plan determined an implant orientation that was less than optimal for a particular patient, guided navigation of that implant will not overcome that deficiency.

Examples of surgical navigation systems are described in U.S. Pat. No. 7,840,256 to Lakin et al., U.S. Pat. No. 8,571,637 to Sheffer et al., U.S. Pat. No. 8,876,830 to Hodorek et al., U.S. Pub. No. 2005/0281465 to Marquart et al., and LS. Pub. No. 2002/0082498 to Wendt et al.

Overview

The present inventors have recognized, among other things, that a problem to be solved can include proper alignment of prosthetic joints within the body after implantation, particularly for a given patient and the patient's post-operative needs. In particular, many surgeons frequently must rely on ad hoc assessments of a patient's joint flexibility based only on observations of the patient flexing of the joint. For example, a surgeon may observe the patient walking or squatting. These assessments do not allow the surgeon to see the actual bone mechanics and therefore often rely on the surgeon's instinct or experience in planning the procedure. Furthermore, these assessments do not take into account a particular patient's intended use of the joint after the procedure, such as golfing, tennis or the like.

The present subject matter can help provide a solution to this problem, such as by providing the surgeon with a pre-operative surgical planning tool that allows the surgeon to visualize the actual joint mechanics, such as by using a visual motion tracking system and a patient-worn body suit. Furthermore, data collected using the body suit can later be used during the arthroplasty procedure to provide real-time feedback to the surgeon in positioning of the prosthetic implant, such as by using an instrument that provides directional feedback to the surgeon.

A method of preparing a surgical plan comprises video capturing a range of motion of an anatomic joint of a patient to obtain a range of motion video, registering the range of motion video to two-dimensional images of a skeleton of the patient, identifying potential impingement and stability issues in the anatomic joint based on the range of motion video, templating a prosthetic implant on two-dimensional images of the anatomic joint using the identified potential impingement and stability issues of the anatomic joint to obtain position and orientation data, and electronically saving the position and orientation data of the prosthetic implant for use with a surgical navigation system.

A system for planning and performing a surgical procedure comprises a motion capture system that records a video of anatomical movements of a patient, an x-ray system that registers the video to a skeletal system of the patient, a electronic modeling system that generates an anatomical model from which position and orientation data for a prosthetic implant can be generated based on the registered video, and a surgical navigation system that correlates the position and orientation data to anatomy of the patient.

This overview is intended to provide an overview of subject matter of the present patent application. It is not intended to provide an exclusive or exhaustive explanation of the invention. The detailed description is included to provide further information about the present patent application.

In the drawings, which are not necessarily drawn to scale, like numerals may describe similar components in different views. Like numerals having different letter suffixes may represent different instances of similar components. The drawings illustrate generally, by way of example, but not by way of limitation, various embodiments discussed in the present document.

DETAILED DESCRIPTION

Figure 1:
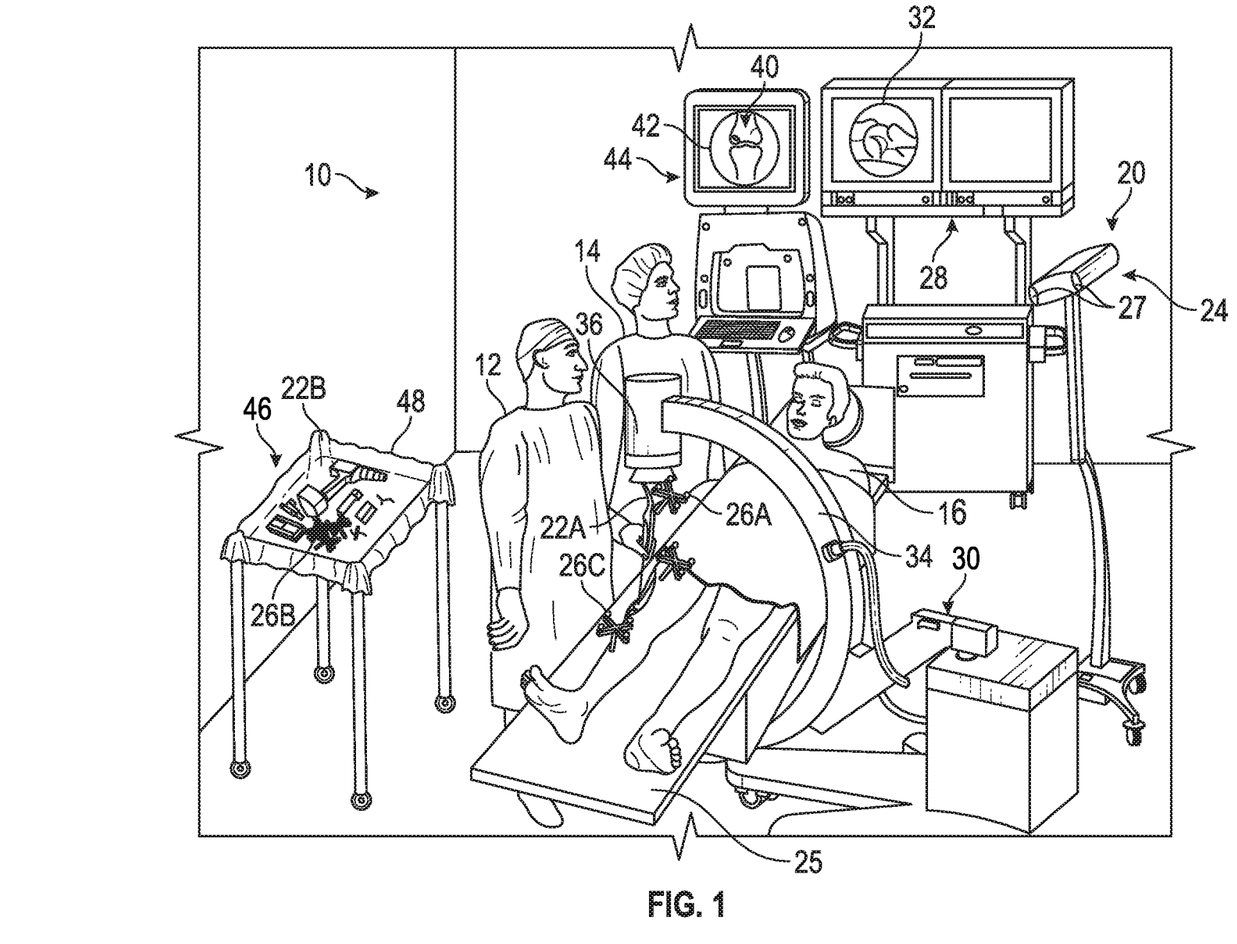
FIG. 1 is a perspective view of an exemplary operating room setup with an assisted surgical navigation system including various tracked devices in conjunction with optical locators.

FIG. 1 shows a perspective view of operating room 10 in which surgeon 12, clinician 14 and patient 16 can be located to perform a medical procedure. Surgical navigation system 20 can also be located in operating room 10 and includes surgical instruments 22A and 22BC and optical locator 24. Surgeon 12 is aided by surgical navigation system 20 in performing various arthroplasty procedures, such as knee and hip replacement surgeries, on patient 16 shown lying on operating table 25. System 20 can also be used to perform any number or other types of procedures, particularly other arthroplasty procedures. One example of a surgical navigation system suitable for use with the present disclosure is described in U.S. Pat. No. 7,840,256 to Lakin et al., which is hereby incorporated herein in its entirety by this reference. Typically, before any procedure is performed, surgeon 12 and clinician 14 can develop a surgical plan that outlines steps to be performed by surgeon 12 and clinician 14 during the procedure. In the present application, the pre-operative surgical plan can include motion-capture video of patient 16 performing various activities.

Figure 3:
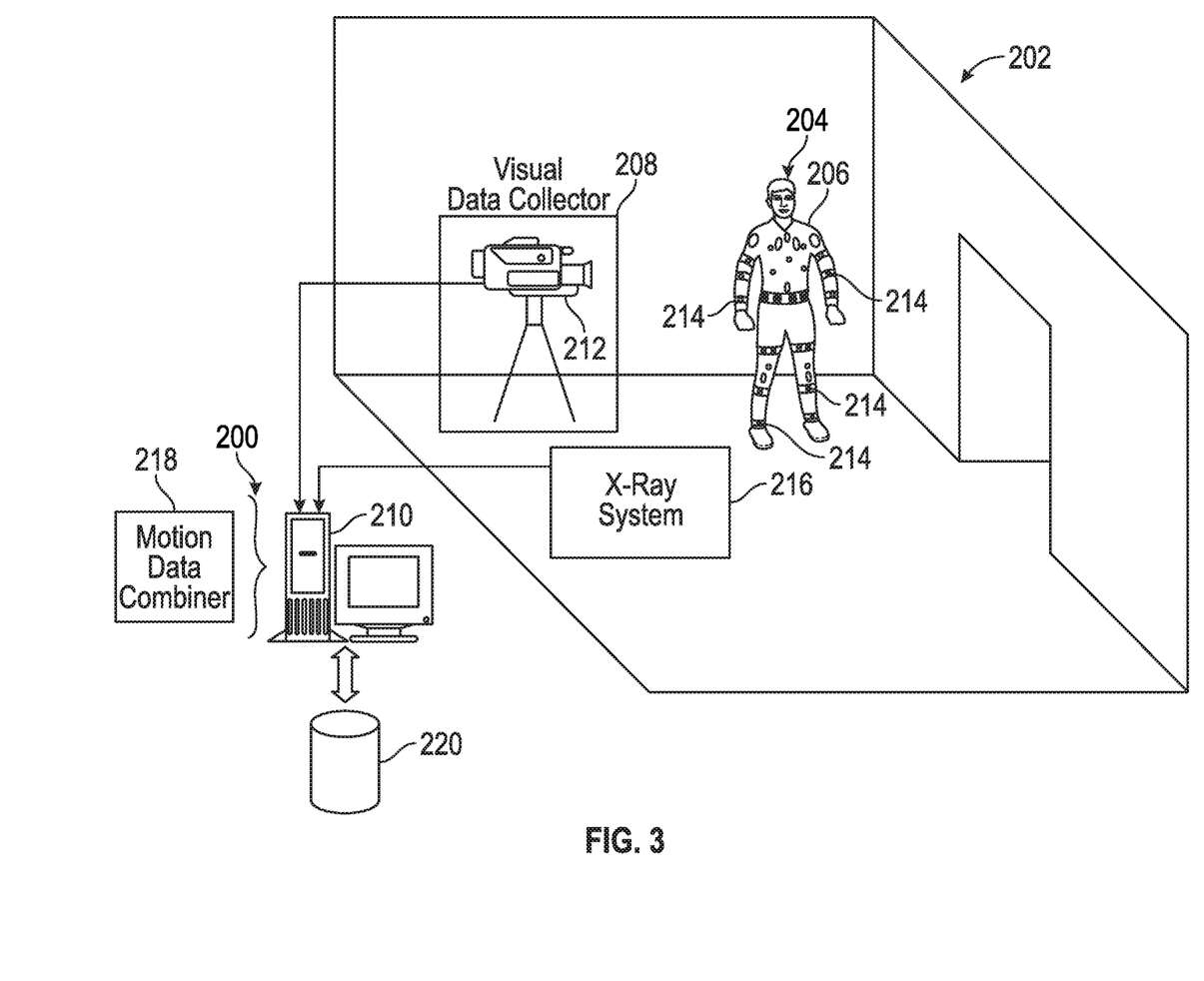
FIG. 3 is a schematic diagram of a visual motion tracking system used to gather patient-specific range of motion and kinesiology data that can be used to determine the surgical plan.

Surgical navigation system 20 can have a tracking system that locates arrays, such as arrays 26A 26C, and tracks them in real-time. Arrays 26A-26C can assist in navigating surgical instruments 22A-22C into particular locations and orientations within operating room 10 using kinematic motion data collected from patient 16 pre-operatively using visual motion tracking system 200 (FIG. 3). The kinematic motion data can assist surgeon 12 and clinician 14 in performing the surgical plan.

To accomplish the tracking, surgical navigation system 20 can include optical locator 24, which can have two CCD (charge couple device cameras 27 that detect the positions of the arrays in space by using triangulation methods. The relative location of the tracked arrays, including the patient's anatomy, can then be shown on a computer display, such as computer display 28 for instance, to assist surgeon 12 during the surgical procedure. The arrays that are typically used include probe arrays, instrument arrays, reference arrays, and calibrator arrays.

Operating room 10 can include an imaging system, such as C-arm fluoroscope system 30 with fluoroscope display image 32 to show a real-time image of the patient's knee on computer display (video monitor) 28. C-arm fluoroscope system 30 includes C-arm 34 to which emitter 36 is mounted. The tracking system can also detect the location of diagnostic scope 22A including its reference array 26A, as well as reference arrays 26B and 26C, which can be attached to the patient's anatomy or another surgical instrument. The relative location of diagnostic scope 22A to the patient's femur can be shown as reference numeral 40 on computer display image 42 of computer display (video monitor) 44. Operating room 10 can also include instrument cart 46 having tray 48 for holding a variety of surgical instruments and arrays, such arrays 26B and surgical instrument 22B. In various examples, surgical instrument 22A can comprise a scope and surgical instrument 22B can comprise a drill, reamer or inserter.

Optical locator 24 is positioned in operating room 10 so that cameras 27 have complete coverage of table 25 and cart 46. Surgical instruments 22A and 22B can be located at various locations throughout operating room 10, such as being held by surgeon 12, or in tray 48 of cart 46.

A representation of the patient's anatomy can be acquired with an imaging system, a virtual image, a morphed image, or a combination of imaging techniques. The imaging system can be any system capable of producing images that represent the patient's anatomy such as a fluoroscope producing x-ray two-dimensional images, computer tomography (CT) producing a three-dimensional image, magnetic resonance imaging (MRI) producing a three-dimensional image, ultrasound imaging producing a two-dimensional image, and the like. A virtual image of the patient's anatomy can be created by defining anatomical points with the surgical navigation system 20 or by applying a statistical anatomical model. A morphed image of the patient's anatomy can be created by combining an image of the patient's anatomy with a data set, such as a virtual image of the patient's anatomy. Some imaging systems, such as C-arm fluoroscope 30, can require calibration. The C-arm can be calibrated with a calibration grid that enables determination of fluoroscope projection parameters for different orientations of the C-arm to reduce distortion. A registration phantom can also be used with a C-arm to coordinate images with the surgical navigation application program and improve scaling through the registration of the C-arm with the surgical navigation system. A more detailed description of a C-arm based navigation system is provided in James B. Stiehl et al., Navigation and Robotics in Total Joint and Spine Surgery, Chapter 3: C-Arm-Based Navigation, Springer-Verlag (2004).

Guiding of surgical instruments 22A and 22B can be conducted by surgeon 12 by looking at video monitors 28 and 44 to direct the instrument in a desired fashion. In particular, surgical instruments 22A and 22B can be used to implant a prosthetic implant in a particular location and orientation relative to the anatomy of patient 16. The location and orientation of the prosthetic implant is determined from the surgical plan, which can be made using kinematic evaluation of the anatomy of patient 16 captured with visual motion tracking system 200 (FIG. 3' Furthermore, the prosthetic implant can be positioned into place and implanted using a navigation assisted surgical instrument having real-time feedback, as described with reference to FIGS. 5A and 5B.

Figure 2:
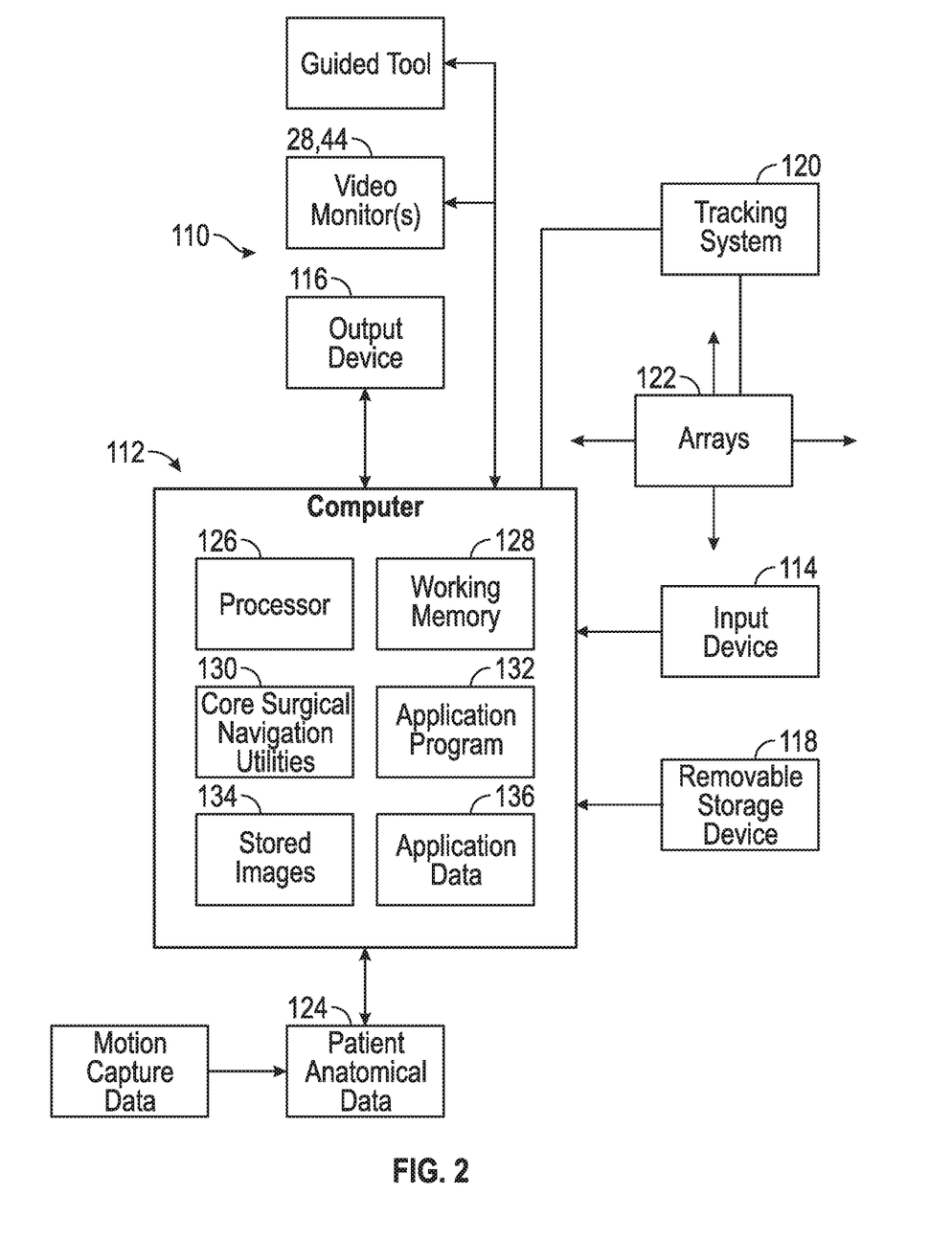
FIG. 2 is a block diagram of components of the assisted surgical navigation system of FIG. 1 showing various inputs and outputs that can be used to implement a surgical plan.

FIG. 2 is a block diagram of an exemplary surgical navigation system embodiment in accordance with the present teachings, such as an Acumen™ Surgical Navigation System, available from EBI, L.P., Parsippany, N.J. USA, a Biomet Company. The surgical navigation system can 110 comprise computer 112, input device 114, output device 116, removable storage device 118, tracking system 120, arrays 122 and patient anatomical data 124, as further described in the brochure Acumen™ Surgical Navigation System, Understanding Surgical Navigation (2003) available from EBI, L.P. The Acumen™ Surgical Navigation System can operate in a variety of imaging modes such as a fluoroscopy mode creating a two-dimensional x-ray image, a computer-tomography (CT) mode creating a three-dimensional image, and an imageless mode creating a virtual image or planes and axes by defining anatomical points of the patient s anatomy. In the imageless mode, a separate imaging device such as a C-arm (e.g., C-arm fluoroscope system 30) is not required, thereby simplifying set-up. The Acumen™ Surgical Navigation System can run a variety of orthopedic applications, including applications for knee arthroplasty, hip arthroplasty, spine surgery, and trauma surgery, as further described in the brochure "Acumen™ Surgical Navigation System, Surgical Navigation Applications" (2003), available from EBI, L.P. A more detailed description of an exemplary surgical navigation system is provided in James B. Stiehl et al., Navigation and Robotics in Total Joint and Spine Surgery, Chapter 1: Basics of Computer-Assisted Orthopedic Surgery (CAOS), Springer-Verlag (2004).

Computer 112 can be any computer capable of properly operating surgical navigation devices and software, such as a computer similar to a commercially available personal computer that comprises processor 126, working memory 128, core surgical navigation utilities 130, application program 132, stored images 134, and application data 136. Processor 126 can be a processor of sufficient power for computer 112 to perform desired functions, such as one or more microprocessors. Working memory 128 can be memory sufficient for computer 112 to perform desired functions such as solid-state memory, random-access memory, and the like. Core surgical navigation utilities 130 are the basic operating programs, and include image registration, image acquisition, location algorithms, orientation algorithms, virtual keypad, diagnostics, and the like. Application program 132 can be any program configured for a specific surgical navigation purpose, such as orthopedic application programs for unicondylar knee ("uni-knee"), total knee, hip, spine, trauma, intramedullary ("IM") nail/rod, and external fixator. Stored images 134 can be those recorded during image acquisition using any of the imaging systems previously discussed (e.g., C-arm fluoroscope system 30). Application data 136 can be data that is generated or used by application program 132, such as implant geometries, instrument geometries, surgical defaults, patient landmarks, and the like. Application data 136 can be pre-loaded in the software or input by the user during a surgical navigation procedure.

Input device 114 can be any conventional computer peripheral, such as a keyboard, mouse, pointing device or camera. Input device 114 can also comprise a microphone for listening to surgeon 12, clinician 14 and patient 16. In one example, the microphone can cause instruments 22A and 22B to generate visual or tactile instructions for surgeon 12 and clinician 14 based on audio calls by either of those persons.

Figure 5A:
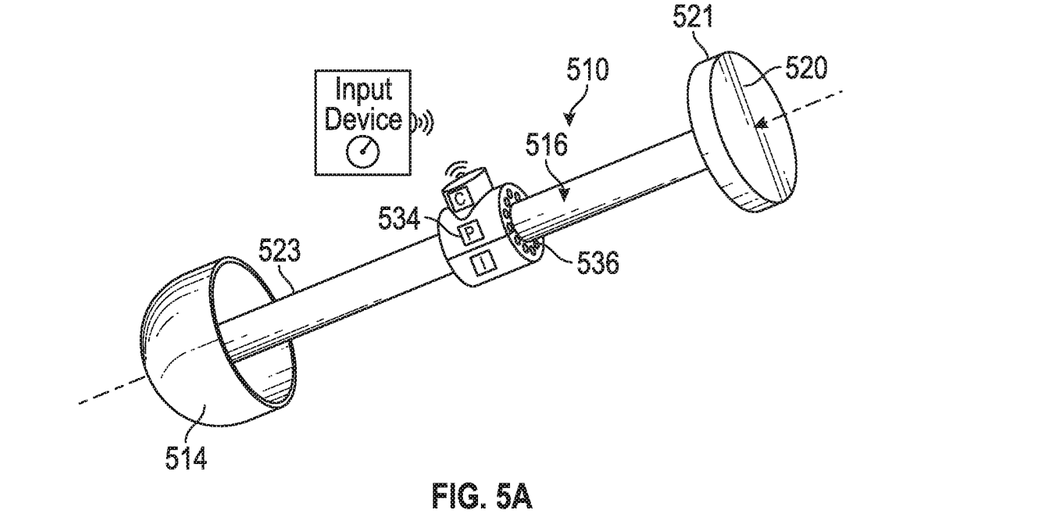
FIGS. 5A and 5B are perspective assembled and exploded views, respectively, of a navigation assisted surgical instrument having real-time feedback.
Figure 5B:
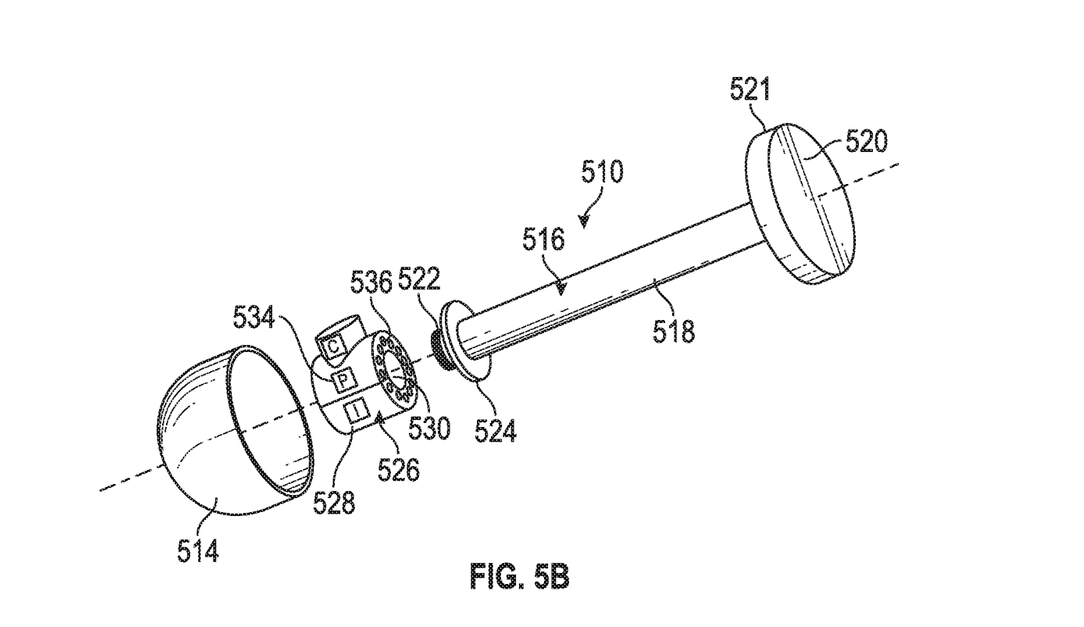
Figure 6:
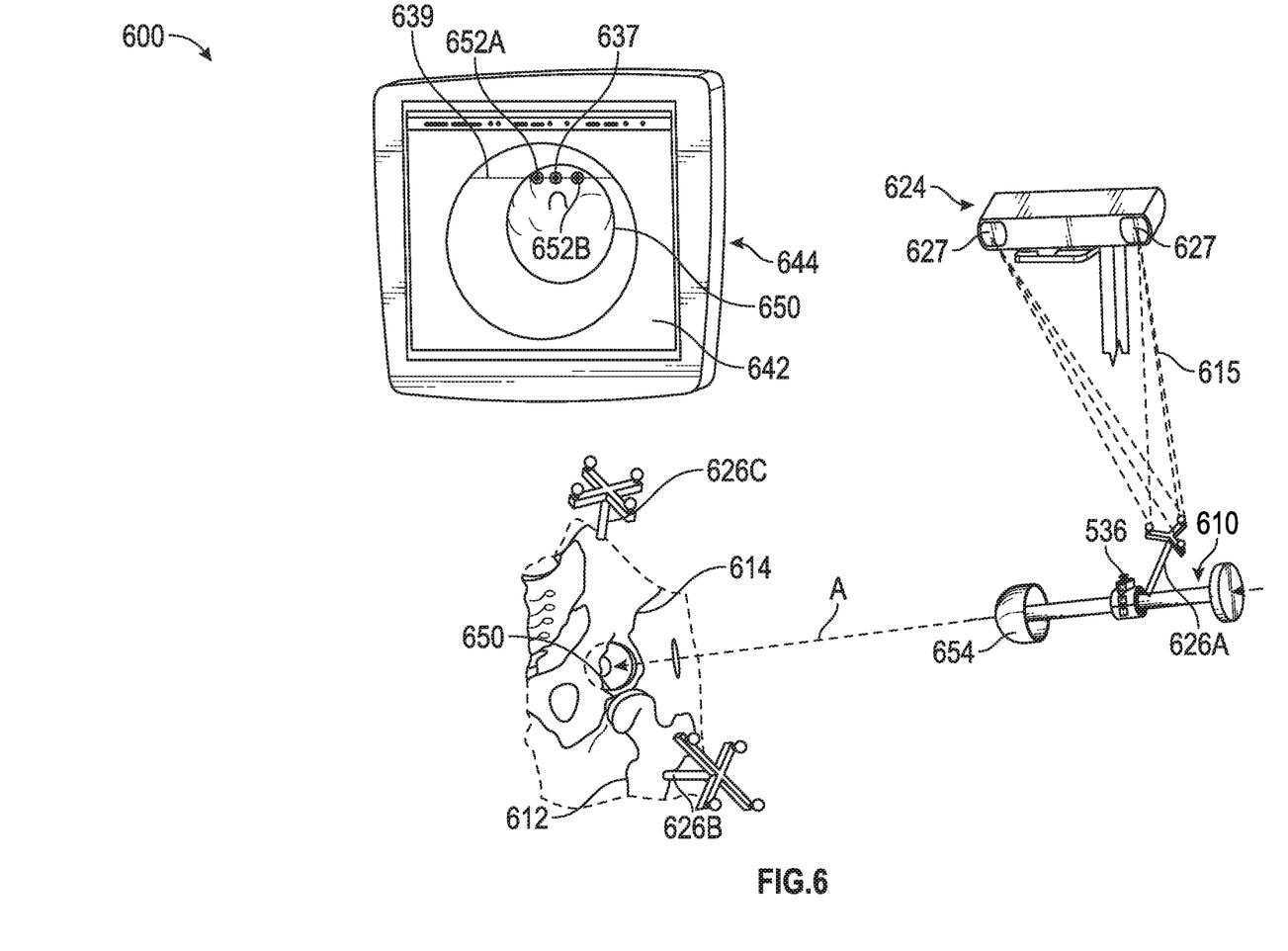
FIG. 6 is a schematic view of a real-time feedback enabled surgical instrument being used to perform a hip arthroplasty procedure in conjunction with a surgical navigation system and patient-specific range of motion and kinesiology data.

Output device 116 can be any device capable of creating an output useful for surgery, such as a visual output and an auditory output. The visual output device can be any device capable of creating a visual output useful for surgery, such as a two-dimensional image, a three-dimensional image, a holographic image, and the like. The visual output device can be a monitor for producing two and three-dimensional images, a projector for producing two and three-dimensional images, and indicator lights. The auditory output can be any device capable of creating an auditory output used for surgery, such as a speaker that can be used to provide a voice or tone output. In particular, output devices can include computer displays 28 and 44 and navigation assisted surgical instruments (guided impactor tools) 510 and 610 (FIGS. 5A-6).

Removable storage device 118 can be any device having a removable storage media that would allow downloading data, such as application data 136 and patient anatomical data 124. The removable storage device can be a read-write compact disc (CD) drive, a read-write digital video disc (DVD) drive, a flash solid-state memory port, a removable hard drive, a floppy disc drive, and the like. Removable storage device 118 can include all of or portions of the aforementioned surgical plan.

Tracking system 120 can be any system that can determine the three-dimensional location of devices carrying or incorporating markers that serve as tracking indicia. An active tracking system has a collection of infrared light emitting diode (ILEDs) illuminators that surround the position sensor lenses to flood 5*a* measurement field of view with infrared light. A passive system incorporates retro-reflective markers that reflect infrared light back to the position sensor, and the system triangulates the real-time position (x, y, and z location) and orientation (rotation around x, y, and z axes) of an array 122 and reports the result to the computer system with an accuracy of about 0.35 mm Root Mean Squared (RMS). An example of a passive tracking system is a Polaris® Passive System and an example of a marker is the NDI Passive Spheres™, both available from Northern Digital Inc. Ontario, Canada. A hybrid tracking system can detect active and active wireless markers in addition to passive markers. Active marker based instruments enable automatic tool identification, program control of visible LEDs, and input via tool buttons. An example of a hybrid tracking system is the Polaris® Hybrid System, available from Northern Digital Inc. A marker can be a passive IR reflector, an active IR emitter, an electromagnetic marker, and an optical marker used with an optical camera.

As is generally known within the art, implants and instruments may also be tracked by electromagnetic tracking systems. These systems locate and track devices and produce a real-time, three-dimensional video display of the surgical procedure. This is accomplished by using electromagnetic field transmitters that generate a local magnetic field around the patient's anatomy. In turn, the localization system includes magnetic sensors that identify the position of tracked instruments as they move relative to the patient's anatomy. By not requiring a line of sight with the transmitter, electromagnetic systems are also adapted for in vivo use, and are also integrable, for instance, with ultrasound and CT imaging processes for performing interventional procedures by incorporating miniaturized tracking sensors into surgical instruments. By processing transmitted signals generated by the tracking sensors, the system is able to determine the position of the surgical instruments in space, as well as superimpose their relative positions onto pre-operatively captured CT images of the patient.

Arrays 122, which can include arrays 26A-26C, can be probe arrays, instrument arrays, reference arrays, calibrator arrays, and the like. Arrays 122 can have any number of markers, but typically have three or more markers to define real-time position (x, y, and z location) and orientation (rotation around x, y, and z axes). An array can comprise a body and markers. The body comprises an area for spatial separation of the markers. In some embodiments, there are at least two arms and some embodiments can have three arms, four arms, or more. The arms are typically arranged asymmetrically to facilitate specific array and marker identification by the tracking system. In other embodiments, such as a calibrator array, the body provides sufficient area for spatial separation of markers without the need for arms. Arrays can be disposable or non-disposable. Disposable arrays are typically manufactured from plastic and include installed markers. Non-disposable arrays are manufactured from a material that can be sterilized, such as aluminum, stainless steel, and the like. The markers are removable, so they can be removed before sterilization.

Planning and collecting patient anatomical data 124 is a process by which a clinician inputs into the surgical navigation system actual or approximate anatomical data. Anatomical data can be obtained through techniques such as anatomic painting, bone morphing, CT data input, and other inputs, such as ultrasound and fluoroscope and other imaging systems. In the present application, patient anatomical data 124 can include kinematic data collected using visual motion tracking systems. Thus, the surgical plan can also include data from a motion capture system, such as video visual motion tracking system 200 and visual data collector 208 (FIG. 3).

Patient anatomical data 124 can also include patient-specific information relating to a particular surgical plan for patient 16. For example, the surgical plan of the surgical procedure can include the planning of various bone resections, sizes and types of implants, and various geometric requirements including relevant dimensions, such as height, width, orientation of particular features, etc. The pre-operative surgical plan can include a recommendation of particular implants and associated instruments to be used in the surgical procedure. The pre-operative surgical plan can be in the form of digital images that can be viewed interactively using a computer modeling software. The pre-operative plan can be a plan devised to obtain a healthy or as close to healthy anatomical orientation after an operative procedure. The healthy anatomy can be based on natural or pre-injury anatomy or mechanically correct or efficient anatomical orientation.

The surgical plan can include, for example, a distal femur with approved resection planes including medial and lateral anterior chamfer planes, medial and lateral anterior cut planes, medial and lateral posterior chamfer planes and medial and lateral posterior cut planes. The surgical plan can include defining a desired varus tilt to the femoral cut plane relative to the implant coordinate frame, or constraining the tibial cut plane in the flexion-extension orientation as well. Likewise, for hip arthroplasty procedures, the surgical plan can include impingement, stability, retroversion, anteversion and pelvic tilt information.

The surgical plan can include instructions for removing one or more osteophytes/protrusions from the patient's anatomy at surgeon-selected locations and depths, which, along with smoothening of the joint surfaces that receive the implant, can parallel the intra-operative joint preparation by the surgeon and improve the actual fit of a surgeon-selected implant, whether patient-specific, semi-custom, or off the shelf.

Cameras 27 can observe the location of arrays 26A-26C, as well as other arrays, within a three-dimensional space defined by the portion of operating room 10 within the viewing area of cameras 27. In other examples, more than one optical locator 24 can be used to determine the three-dimensional space. Positional information obtained from arrays 26A-26C corresponding to the instruments or tools or patient anatomy associated with or attached to each array is used by computer 112 determine an instruction that can be sent to a guided tool, such as guided impactor tools 510 and 610 (FIGS. 5A-6). In particular, computer 112 compares or correlates the location of one or more instruments or tools within the three-dimensional space and can then consult the surgical plan to determine at which step the surgical procedure is at in the surgical plan. From that comparison or correlation, computer 112 can cause the guided instrument (e.g., guided impactor tools 510 and 610) to vibrate to provide haptic feedback, or to emit a sound or visual indicator that guides surgeon in performing a particular step or process in the surgical plan within the three-dimensional space.

FIG. 3 shows a schematic view of visual motion tracking system 200 that can be used to pre-operatively plan an arthroplasty procedure. Exemplary environment 202 (e.g., surgeon office, outpatient clinic, hospital, etc) is illustrated for collecting visual and physical motion information from patient 204 wearing the body suit 206. While environment 202 is depicted as an interior location, in some arrangements the environment may be external (e.g., located outside) or a combination of two types of locations (e.g., for performances that include the patient moving from an interior location to an exterior location). One example of a visual motion tracking system is described in U.S. Pat. No. 9,142,024 to Sullivan et which is assigned to Lucasfilm Entertainment Company and hereby incorporated herein in its entirety by this reference.

To collect visual information produced by patient 204, visual data collector 208 and a computer system 210 can be included in the visual motion tracking system 200. In this particular arrangement, visual data collector 208 can include a camera 212 that is capable of capturing multiple frames of visual information. In general, each frame can be considered as visual sample of a pose of patient 204 as represented by markers 214 included in body suit 204. From the information captured by camera 212, the pose can be represented as a set of numerical values that describe how patient 204 has moved at a particular instance in time. For example, the pose could include such numerical values that represent the angle of the hip bones of patient 204, as well as other joints and bones, the patient's global position and global orientation relative to environment 202. Typically, the numerical values that represent the pose are relative to a predefined canonical pose. For example, a pose in which patient 202 is standing with both arms pointing horizontally outward (referred to as a "T" pose) can be defined as a canonical pose. While one camera 212 is illustrated as being included in the visual motion tracking system 200, two or more cameras which are typically synchronized for image capture) can also be included for capturing visual information from different perspectives. To use the visual data captured by camera 212, computer system 210 executes operations that include receiving, processing and outputting data. In some arrangements, computer system 210 can also execute operations to control one or more operations of the camera(s) (e.g., control data capture rate, adjust camera orientation, etc.). Operations of computer system 210 can also include computing the location of the camera and its visual properties, such as the camera's field of view, lens distortion, and orientation, while a sequence of images is being recorded. For example, operations of computer system 210 can derive the position of camera 212 given enough markers 214 and information associated with the markers, such as the number, identification, and position of markers 214 captured by camera 212.

From markers 214 or other features of body suit 206 or features of patient 204, one or more cameras (e.g., camera 206) record the motion of the actor. To determine the pose of patient 204, computer system 210 executes operations to identify each marker 214 that is visible in the captured 2D data and assigned a correspondence to the particular marker of body suit 206 (referred to as tracking). Next, one or more techniques can be used by computer system 210 identify the pose of patient 206 (referred to as solving), for example, by finding a pose that minimizes re-projection error of an estimated 3D position of the markers onto the captured image from camera 212.

Along with collecting the images from patient 204 collected using visual data collector 208, information is also collected from patient using x-ray system 216. In particular, patient 204 can be x-rayed wearing body suit 206 such that markers 214 are shown relative to the anatomy of patient 204. In various examples, x-ray images of patient 204 are taken in various orthogonal directions relative to patient 214 in the "T" pose.

Similar to visual data collector 208, computer 110 can be used to collect digital images of patient 204 wearing body suit 206 with markers 214. By processing the data from x-ray system 216 along with data from visual data collector 208, motion of patient 204 relative to markers 114 can be correlated to motion of bones, e.g., femur, tibia, pelvis, of patient 204 via mapping to markers 214. The x-ray image data can be calculated from the data that corresponds in time to the images captured by camera 212.

By producing these two synchronized data sets, the anatomy data can be combined with the image data to view the anatomy performing particular activities, such as daily living activities (e.g., sitting and bending), athletic activities (e.g., golf, and tennis), yoga, exercise, running and the like. The x-ray images can be used to produce a virtual representation of patient 204 that can, in turn, be used to describe the motion of patient 204 by using the video data to approximate the true kinematics of patient 204 using the x-ray data. Each joint of patient 204, such as the shoulder, knee, hip, etc., need not be recorded, but it is useful to capture the range of motion of the joint of interest while it is moving in conjunction with other joints.

To combine and use the visual data provided by camera 212 and x-ray system 216, computer system 210 can execute one or more processes. For example, motion data combiner 218 can be executed for combining the data sets and using the data sets to form a skeleton that virtually represents the movement of patient 204. To assist with execution, storage device 220 (e.g., hard drive or CD-ROM) is in communication with computer system 210 and can be used for storing and retrieving data. In various examples, storage device 220 can comprise one or more of the storage devices of surgical navigation system 110, such as removable storage device 118 or working memory 128, onto which patient anatomical data 124 may be stored.

Along with components (e.g., interface cards) for receiving user input and data from various sources (e.g., camera 212, x-ray data collector 216, the Internet and other computer systems), computer system 210 can also include memory (not shown) and one or more processors (also not shown) to execute processing operations. Storage device 220 is capable of storing data (e.g., visual data and x-ray data) and providing the stored data to assist production of a surgical plan for patient 204.

Various operations can be executed to combine the x-ray data and the visual data. For example, one or more actions from patient 204 can also be used as a synchronizing trigger. For example, patient 204 may perform a predefined action (e.g., waving both arms and jumping up and down) that is clearly identifiable in each data set and used to accurately align the data sets.

The combined data allows a surgeon, e.g., surgeon 12, to evaluate the particular performance of the anatomy of the patient, e.g., patient 16. Specifically, the surgeon can look for potential impingement areas in a joint, such as at the acetabulum in a hip joint, or evaluate potential stability issues in a joint. Such information cannot be readily ascertained by merely observing the patient perform generic motions. With the combined motion and x-ray data, the surgeon can add specific details to the surgical plan that might not otherwise have been determined and that might lead to a better post-operative experience by the patient. In particular, the combined motion and x-ray data can lead the surgeon to make better decisions about implant position and alignment, such as better acetabular cup placement and femoral component orientation in a hip arthroplasty.

Figure 4:
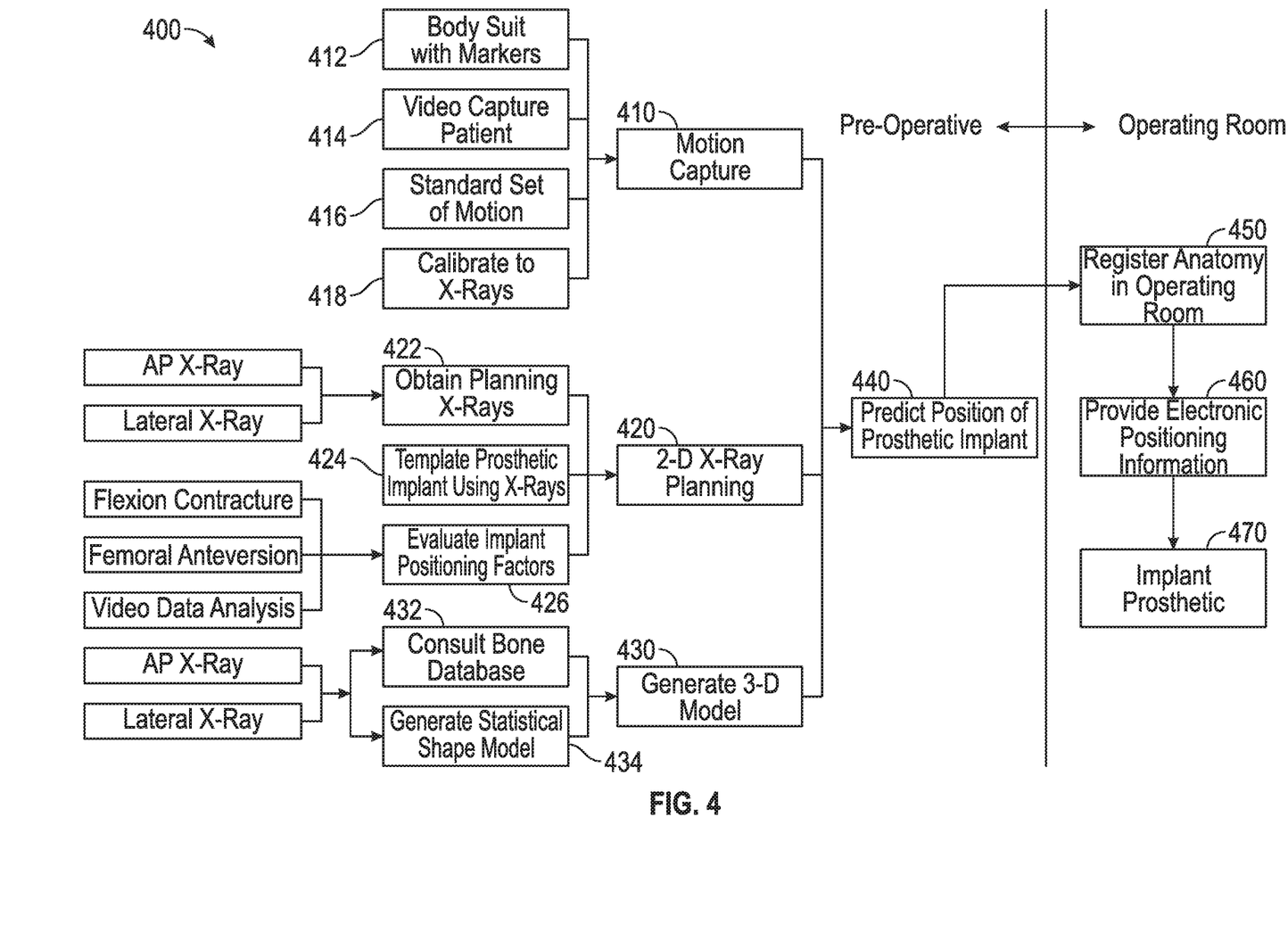
FIG. 4 is a block diagram showing various data collection inputs and steps that are used to determine and implement the surgical plan.

FIG. 4 is block diagram 400 showing various data collection inputs and steps that are used to determine and implement a surgical plan for a hip arthroplasty. At input 410, the functional range of motion of a hip joint of patient 16 can be captured pre-operatively and registered to a skeleton. At input 420, various two-dimensional images can be used to template prosthetic implant data. At input 430, statistical data can be used to model the anatomy of patient 16 to assist in placement of the prosthetic implant by surgeon 12. At step 440, the type, size, location and orientation of the prosthetic implant can be predicted.

At step 450, during surgery, the anatomy of patient 16 can be registered to surgical navigation systems. At step 460, various electronic positioning information can be provided to the surgeon during surgery using various guided instruments. Finally, at step 470, the surgeon can use the electronic positioning information to implant the prosthetic device, as discussed with reference to FIG. 6.

At step 412, patient 16 is outfitted with a body suit having markers. At step 414, the patient is video recorded wearing the body suit. In one example, system 200 of FIG. 3 is used, as discussed, to capture motion data of patient 16 using body suit 2016 with markers 214. In another example, patient 16 can be video recorded using a smart phone or tablet using a specific software application. Patient 16 can wear a suit having an array of markers, such as visual markers and/or radiopaque markers, that are identifiable by the software application in the video. In any embodiment, the suit can be fairly skin tight, that is, it can be stretchable to conform to the contours of the body of patient 16 so that the markers will be closely associated with the skeletal structure of patient 16. As such, in various examples, markers can be placed on opposite sides of a joint, such as on the pelvis and on the femur to record motion associated with a hip joint. In another example, the posture of patient 16 can be used to correlate and combine the implant to the anatomy and the anatomy to the visual markers.

At step 416, patient 16 can perform a set of movements to capture the range of motion of the patient. For example, patient 16 can perform a standard set of "daily living" activities, such as bending, sitting and the like. In additional examples, patient 16 can be video recorded performing activities to be specifically performed by patient 16. For example, patient 16 can be video recorded performing sports activities (e.g., golf and tennis), yoga, exercise, running, and various other activities, athletic or not. Thus, patient-specific impingement and stability issues in a particular joint can be observed and evaluated when sizing a prosthetic implant and subsequently planning or predicting a location and orientation for the implant.

At step 418, orthogonal x-rays of patient 16 wearing the suit are obtained in order to calibrate the video motion to the bones of patient 16. For example, a marker ball having a known geometry can be positioned within the field of view of the x-ray at the level of the bones so that the scale of the x-ray can be determined later. The two dimensional x-ray images can subsequently be used by the surgeon to template hypothetical implant types, sizes and location on the anatomy of the patient. The templating can further include determining locations for incisions, cuts, resections and the like on the anatomy of patient 16.

Steps 412-418 can be performed by a clinician or technician, or by a surgeon at a hospital or other out-patient facility. Steps 412-418 are easy to perform, inexpensive and need not be conducted in a sterile or surgical environment. Thus, other more expensive and more demanding procedures, such as MRI procedures, can be avoided.

At step 422, the patient can be x-rayed to plan implant component positions. The x-rays can be performed using the same, or an identical, calibration marker ball as in previous steps. Conventional Anterior-Posterior and Lateral standing X-rays can be obtained of patient 16. These x-ray images can be used prior to surgery to determine a prosthetic implant and its location relative to the patient's bones using the range of motion knowledge gained earlier in steps 412-418.

At step 424, surgeon 12 can template the anatomy of patient 16 using the x-ray images to determine the desired prosthetic implant for the procedure. The size of the implants can be determined by using the scaling factor determined by the calibration marker ball. Surgeon 12 can take measurements of the bones that cat be used to determine implant size and the location and depth of various cuts and incisions to be performed during the procedure.

At step 426, surgeon 12 can evaluate generic and patient-specific implant positioning factors in performing the templating. For example, conventional flexion contracture and femoral anteversion evaluations can be performed for a hip arthroplasty. Additionally, the patient-specific range of motion data collected in steps 412-418 can be used. For example, if a patient wants to be able to perform a particular activity requiring a particular range of motion, surgeon 12 can make sure the predicted placement for the prosthetic implant will allow patient 16 to perform that activity. For example, if a particular yoga position requires patient to move femur into a particular flexion and abduction position, the predicted placement for the prosthetic implant can accommodate that particular position, such as by avoiding impingement or stability issues for patient 16 while in that position.

At step 432, various databases having anatomical bone data can be consulted. For example, one or more of a plurality of modeled bones from a bone database can be fit to the measured dimensions of the bones of patient 16 taken at step 424. In one example, a precision medicine initiative (PMI) bone database can be consulted. At step 434 three-dimensional models of the bones of patient 16 can be generated using statistical shape models. The anterior pelvic plane from the statistical shape model can be used as a reference for prosthetic implant positioning, e.g. of the femoral cup. The statistical shape model(s) can be used by surgeon 12 to visualize the arthroplasty procedure and improve the position and orientation of the implant relative to a three-dimensional bone without having to have an MRI image or another three-dimensional image generated preoperatively.

At step 440, the final implanted position and orientation of the selected prosthetic implant is determined. For a hip arthroplasty, the relative positions of the cup and femoral component can be predicted with anatomical landmarks. For example, the cup posterior rim can be determined to be 3 mm proud compared to the acetabular posterior rim, and the femoral component lateral shoulder can be determined to be 11 mm distal to the tip of the greater trochanter.

At step 450, during surgery, the anatomy of patient 16 is registered to the three-dimensional space of operating room 10. The pelvis and femur are registration in operating room 10, as previously described herein, after access to the joint has been achieved. For a total hip replacement, markers, such as arrays 26C, can be placed on the pelvis and femur of patient 16 inside the surgical field of view of cameras 27. The markers are fixated to bony points so as to not move relative to the bones and distort the positional information. In particular, using surgical navigation system 20, the bones to be operated on can be marked with electronic identifiers on an x-ray image of patient 16 obtained with C-arm fluoroscope system 30. Those locations are then correlated to the three-dimensional space using optical locator 24. For example, in a hip arthroplasty, the inside diameter of the acetabulum can be "painted" with electronic markers using surgical navigation system 20 to define an acetabular position to be linked to x-ray images. The electronic markers can be placed using a roller ball computer peripheral to accelerate the registration of acetabular points. The registration process can include registering femoral or pelvic landmarks to link femoral and pelvic anatomy to the x-ray images.

At step 460, electronic positioning information generated at step 440 for planned cup and femoral component can be matched up in operating room 10 to images on video monitors 28 and 44 and other components. The positioning information is used to guide surgical instruments, such as scope 22A, drill 22B or guided impactor tool 510, as described below when implanting the prosthetic at step 470.

FIGS. 5A and 5B are perspective assembled and exploded views, respectively, of navigation assisted surgical instrument 510 having real-time feedback. In the described embodiment, navigation assisted surgical instrument 510 comprises an implanting assembly such as a guided impactor tool. Implanting assembly 510 can be used for implanting any suitable prosthetic member. In the embodiments illustrated, implanting assembly 510 is used to implant acetabular cup 514. Implanting assembly 510 can be used to implant acetabular cup 514 within acetabulum 650 of pelvis 614 (FIG. 6) of patient 16 (FIG. 1). Thus, implanting assembly 510 can be used in a process for replacing a hip joint with a prosthetic hip joint assembly.

Implanting assembly 510 is described in greater detail in U.S. Pat. No. 8,167,823 to Nycz et al., which is hereby incorporated herein in its entirety by this reference. Features and operation of implanting assembly 510 relative to the present application are summarized below.

Implanting assembly 510 can include impactor tool 516. Generally, impactor tool 516 can include elongated shaft 518 having an enlarged striking plate or head 520 at a proximal or first end 521. Shaft 518 can be longitudinally straight so as to define an axis A. Distal or second end 523 of shaft 518 can include a coupling mechanism as shown in phantom in FIG. 2. In some embodiments, the coupling mechanism can include a thread (shown in phantom at 522) and a projection (shown in phantom at 524). Thread 522 can enable shaft 518 to be removably coupled to acetabular cup 514 in a corresponding threaded hole (not shown) in acetabular cup 514.

As will discussed below with reference to FIG. 6, in order to implant acetabular cup 514 in patient 16, a load $F_i$ (FIG. 5A) is applied to head 520 of impactor tool 516. The surgeon can apply the load $F_i$ with a mallet or other manual tool or with an automated tool. Shaft 518, in turn, transfers the load $F_i$ along the axis A to acetabular cup 514. Thus, acetabular cup 514 is driven progressively into acetabulum 650 of pelvis 614 (FIG. 6) of patient 16 (FIG. 1) with each application of the load $F_i$.

Implanting assembly 510 can also include implanting apparatus 526. Implanting apparatus 526 can include housing 528. Housing 528 can be substantially cylindrical in shape with passage 530 extending parallel and concentric to the axis A. Passage 530 receives shaft 518 to fixedly couple housing 528 to tool 516 in a fixed position relative to the axis A. First and second portions 532a, 532b of housing 528 can separate along seam 531 to remove housing 528 from shaft 518.

Implanting apparatus 526 can include an orientation sensor 534. Orientation sensor 534 can be encapsulated within housing 528. In other embodiments, orientation sensor 534 is remote from the impactor tool 16. Orientation sensor 534 can detect an actual orientation of impactor tool 516. More specifically. Orientation sensor 534 can be an accelerometer that is able to detect the orientation of impactor tool 516 relative to a reference vector. In some examples, orientation sensor 534 detects the vector of the force of gravity as a reference vector to detect the orientation of impactor tool 516 in space and relative to the patient. Orientation sensor 534 detects the orientation of the axis A relative to the vector of the force of gravity to detect the orientation of tool 516. In some examples, orientation sensor 534 detects acceleration about three separate orthogonal axes X, Y, Z relative to operating room 10 (FIG. 1) using array 626A (FIG. 6) in order to detect the orientation of impactor tool 516. Orientation sensor 534 detects the orientation of the axis A relative to the coordinate system X, Y, Z. It will be appreciated that orientation sensor 534 could be of any suitable type other than an accelerometer. Also, it will be appreciated that orientation sensor 534 can be an accelerometer that detects accelerations about any number (e.g., two) of axes.

Furthermore, implanting apparatus 526 can include orientation feedback device 536. Feedback device 536 can be encapsulated within housing 528, or in other embodiments, feedback device 536 is remote from housing 528. Orientation feedback device 536 can selectively provide an orientation feedback signal when the actual orientation of impactor tool 516 is substantially equal to a predetermined target orientation. The feedback signal provided by orientation feedback device 536 automatically indicates to the surgeon that impactor tool 516 is in the target orientation such that cup 514 can be properly positioned and implanted for added convenience and accuracy.

Orientation feedback device 536 can include an audible feedback device that emits an audible feedback signal. For example, the audible feedback device can include a speaker that emits a preprogrammed sound when impactor tool 516 is in the target orientation. Furthermore, orientation feedback device 536 can include a visual feedback device that emits a visual feedback signal. For example, the visual feedback device can include one or more lights, such as LED lights, for emitting a preprogrammed light pattern when impactor tool 516 is in the target orientation. Additionally, orientation feedback device 536 can include a tactile feedback device that selectively emits a tactile feedback signal when impactor tool 516 is in the target orientation. For example, the tactile feedback device can include a vibration motor that selectively vibrates housing 528 and impactor tool 516 when impactor tool 516 is in the target orientation. It will be appreciated that orientation feedback device 536 can provide any suitable feedback signal. Also, it will be appreciated that the feedback signal can be seen, heard, and felt simultaneously, and this redundancy can increase accuracy and convenience.

Navigation assisted surgical instrument 510 can be used with predicted position and orientation information obtained at step 440 of FIG. 4 to implant a prosthetic device at steps 450-470 of FIG. 4.

FIG. 6 is a schematic view of surgical navigation system 600 including real-time feedback enabled surgical instrument 610 being used to perform a hip arthroplasty procedure on femur 612 and pelvis 614. System 600 also includes optical locator 624 (which may comprise optical locator 24 of FIG. 1 in an example) and cameras 627 (e.g. cameras 27). Surgical instrument 610 includes marker array 626A, while femur 612 includes marker array 626B and pelvis includes marker array 626C.

As a surgeon moves surgical instrument 610 relative to femur 612 and pelvis 614, the tracking system locates and tracks marker arrays 626A-626C in real-time (see the optical path/measurement field of the tracking system represented by the dashed lines). To accomplish this, cameras 627 of optical locator 624 detect the position of marker arrays 626A-626C in space by using triangulation methods. The relative location of marker arrays 626A-626C are then shown on surgical plan image 642 on computer display 644 (e.g. computer display 44).

The tracking system detects the location of surgical instrument 610, in this case an acetabular impactor, relative to femur 612 and pelvis 614 by referencing the position of marker arrays 626A as it moves with respect to reference arrays 626B and 626C, which are fixably attached to the patient. As shown in FIG. 6, the position of surgical instrument 610 is displayed on surgical plan image 642 as impact location icon 637. Impact location icon 637 can have the appearance of a crosshairs, while target sites 652a and 652b can have the appearance of bullseyes. According to this illustration, impact location icon 637 is shown positioned over the acetabulum 650 of pelvis 614. Target sites 652a and 652b represent different impact sites for cup 654 on acetabulum 650, for different planned locations of cup 654 determined in the surgical plan.

By viewing impact location icon 637 on surgical plan image 642, surgeon 16 can determine which direction to move surgical instrument 610 so that it aligns with either of surgical target sites 652a or 652b on images of femur 612 and pelvis 614 in image 642. For instance, in this illustrated embodiment, surgeon 16 must move impactor 610 immediately to the right along line 639 to align impact location icon 637 with surgical target site 652b.

To locate surgical target site 652b, the point on acetabulum 650 can be referenced by surgeon 16 and/or the computer tracking system, such as during step 450 of FIG. 4. In certain exemplary embodiments, surgical target site 652b is identified by modeling the acetabulum through a "painting" or imaging technique which allows the computer system to determine the proper impact point, such as the center, of acetabulum 650. No matter how surgical site 652b is determined, if it is later found to be inappropriate for conducting the surgery (i.e., not properly aligned), surgeon 16 is always able to override the site and rely on the computer for orientation only.

Furthermore, as discussed above, surgical instrument could provide feedback to surgeon 10 using various output means. In particular orientation feedback device 536 can provide audible, visual and tactile feedback. In one example, feedback device 536 can include different lights which surgeon 16 can use to guide cup 654 into acetabulum 650 along axis A. For example, feedback device 536 can include red, yellow and green lights that indicate to surgeon 16 how close to impact location icon 637 the alignment of impactor 610 is. A green light can indicate proper alignment, a red light can indicate improper alignment, and a yellow light can indicated that alignment is within a certain threshold limit. Proper alignment can be described as when axis A of impactor 610 is aligned perpendicular to the impact site represented by impact location icon 637.

In one example, impact location icon 637 and target sites 652a and 652b can be projected onto a heads-up display worn by surgeon 16. For example, rather than surgeon 16 having to look up at computer display 644, surgeon 16 can wear a helmet having a screen in the line of sight of surgeon 16 onto which icon 637 and target sites 652a and 652b can be projected. In one example, the heads-up display can comprise a Google Glass system.

In another example, surgical plan image 642 from computer display 644 can be projected on a mobile screen positionable within operating room 10. For example, the portable screen can comprise a component of a smart phone or tablet computer that receives or has stored therein the surgical plan.

With the systems and methods described herein, surgeon 16 is better able to perform surgical operations. In particular, the entire surgical procedure can be more accurately and more rapidly completed, as each successive step can be completed in in less time and with more precision. The finally implanted prosthetic device can be implanted to avoid impingement and stability issues. In particular, pre-operatively obtained kinematic motion capture video and x-ray images can be used to identify potential impingement and stability issues for prosthetic devices related to patient-specific activities to be performed by the patient. As such a surgical plan can be implemented to avoid implant orientations that might give rise to impingement and stability issues. The proper surgically planned implant alignment can be ensured using guided, real-time feedback enabled surgical tools that are guided using data collected preoperatively.

Various Notes & Examples

Example 1 can include or use subject matter such as a method of preparing a surgical plan, the method comprising: video capturing a range of motion of an anatomic joint of a patient to obtain a range of motion video; registering the range of motion video to images of a skeleton of the patient; identifying potential impingement and stability issues in the anatomic joint based on the range of motion video; templating a prosthetic implant on two-dimensional images or a three-dimensional model of the anatomic joint using the identified potential impingement and stability issues of the anatomic joint to obtain position and orientation data; and electronically saving the position and orientation data of the prosthetic implant for use with a surgical navigation system.

Example 2 can optionally include, or can optionally be combined with the subject matter of Example 1 to optionally include video capturing the range of motion of the anatomic joint comprises videotaping the patient wearing a body suit having visual markers and/or radiopaque markers.

Example 3 can include, or can optionally be combined with the subject matter of one or any combination of Examples 1 or 2 to optionally include registering the range of motion video to the skeleton of the patient comprising obtaining orthogonal x-rays of the patient wearing the body suit having the visual and/or radiopaque markers.

Example 4 can include, or can optionally be combined with the subject matter of one or any combination of Examples 1-3 to optionally include video capturing the range of motion comprising videotaping the patient wearing the body suit having visual markers while performing a patient-specific activity that flexes the anatomic joint.

Example 5 can include, or can optionally be combined with the subject matter of one or any combination of Examples 1-4 to optionally include templating, the prosthetic implant comprises marking on a digital copy of the two-dimensional images locations for anatomic incisions on anatomy of the patient.

Example 6 can include, or can optionally be combined with the subject matter of one or any combination of Examples 1-5 to optionally include the two-dimensional images comprising orthogonal x-ray images of the skeleton of the patient taken without the body suit.

Example 7 can include, or can optionally be combined with the subject matter of one or any combination of Examples 1-6 to optionally include generating an electronic three-dimensional model of the anatomic joint of the patient based on statistical data and annotating the three-dimensional model with the implant location and orientation.

Example 8 can include, or can optionally be combined with the subject matter of one or any combination of Examples 1-8 to optionally include templating the prosthetic implant comprising locating an image of the prosthetic device on the three-dimensional model.

Example 9 can include, or can optionally be combined with the subject matter of one or any combination of Examples 1-9 to optionally include registering the anatomic joint of the patient in an operating room to images of the patient using a surgical system having a positioning system.

Example 10 can include, or can optionally be combined with the subject matter of one or any combination of Examples 1-9 to optionally include providing electronic positioning information to a surgical device in order to locate the prosthetic implant at a location and orientation from the position and orientation data.

Example 11 can include, or can optionally be combined with the subject matter of one or any combination of Examples 1-10 to optionally include providing electronic positioning information further comprising displaying color-coded visual indicators on an inserter indicate alignment of the inserter relative to the location and orientation of the prosthetic implant.

Example 12 can include, or can optionally be combined with the subject matter of one or any combination of Examples 1-11 to optionally include providing the electronic positioning information further comprising displaying the location and orientation of the prosthetic implant onto a display of a mobile device located in the operating room.

Example 13 can include, or can optionally be combined with the subject matter of one or any combination of Examples 1-12 to optionally include providing the electronic positioning information further comprising projecting the location and orientation of the prosthetic implant onto a heads-up display worn by a surgeon in the operating room.

Example 14 can include or use subject matter such as a system for planning and performing a surgical procedure, the system comprising: a motion capture system that records a video of anatomical movements of a patient; an x-ray system that registers the video to a skeletal system of the patient; an electronic modeling system that generates an anatomical model from which position and orientation data for a prosthetic implant can be generated based on the registered video; and a surgical navigation system that correlates the position and orientation data to anatomy of the patient.

Example 15 can include, or can optionally be combined with the subject matter of Example 14 to optionally include a surgical instrument is electronically guided by the surgical navigation system based on the position and orientation data.

Example 16 can include, or can optionally be combined with the subject matter of one or any combination of Examples 14-15 to optionally include a motion capture system comprising: a video camera; and a body suit having markers.

Example 17 can include, or can optionally be combined with the subject matter of one or any combination of Examples 14-16 to optionally include an electronic modeling system that generates a statistical shape model based on a bone database.

Example 18 can include, or can optionally be combined with the subject matter of one or any combination of Examples 14-17 to optionally include a surgical navigation system comprising a tracking system having an optical locator and a plurality of arrays.

Example 19 can include, or can optionally be combined with the subject matter of one or any combination of Examples 14-18 to optionally include a wearable heads-up display onto which the position and orientation data can be projected.

Each of these non-limiting examples can stand on its own, or can be combined in various permutations or combinations with one or more of the other examples.

The above detailed description includes references to the accompanying drawings, which form a part of the detailed description. The drawings show, by way of illustration, specific embodiments in which the invention can be practiced. These embodiments are also referred to herein as "examples." Such examples can include elements in addition to those shown or described. However, the present inventors also contemplate examples in which only those elements shown or described are provided. Moreover, the present inventors also contemplate examples using any combination or permutation of those elements shown or described (or one or more aspects thereof), either with respect to a particular example (or one or more aspects thereof), or with respect to other examples (or one or more aspects thereof) shown or described herein.

In the event of inconsistent usages between this document and any documents so incorporated by reference, the usage in this document controls.

In this document, the terms "a" or "an" are used, as is common in patent documents, to include one or more than one, independent of any other instances or usages of "at least one" or "one or more." In this document, the term "or" is used to refer to a nonexclusive or, such that "A or B" includes "A but not B," "B but not A," and "A and B," unless otherwise indicated. In this document, the terms "including" and "in which" are used as the plain-English equivalents of the respective terms "comprising" and "wherein." Also, in the following claims, the terms "including" and "comprising" are open-ended, that is, a system, device, article, composition, formulation, or process that includes elements in addition to those listed after such a term in a claim are still deemed to fall within the scope of that claim. Moreover, in the following claims, the terms "first," "second," and "third," etc. are used merely as labels, and are not intended to impose numerical requirements on their objects.

Method examples described herein can be machine or computer-implemented at least in part. Some examples can include a computer-readable medium or machine-readable medium encoded with instructions operable to configure an electronic device to perform methods as described in the above examples. An implementation of such methods can include code, such as microcode, assembly language code, a higher-level language code, or the like. Such code can include computer readable instructions for performing various methods. The code may form portions of computer program products. Further, in an example, the code can be tangibly stored on one or more volatile, non-transitory, or non-volatile tangible computer-readable media, such as during execution or at other times. Examples of these tangible computer-readable media can include, but are not limited to, hard disks, removable magnetic disks, removable optical disks (e.g., compact disks and digital video disks), magnetic cassettes, memory cards or sticks, random access memories (RAMs), read only memories (ROMs), and the like.

The above description is intended to be illustrative, and not restrictive. For example, the above-described examples (or one or more aspects thereof) may be used in combination with each other. Other embodiments can be used, such as by one of ordinary skill in the art upon reviewing the above description. The Abstract is provided to comply with 37 C.F.R. § 1.72(b), to allow the reader to quickly ascertain the nature of the technical disclosure. It is submitted with the understanding that it will not be used to interpret or limit the scope or meaning of the claims. Also, in the above Detailed Description, various features may be grouped together to streamline the disclosure. This should not be interpreted as intending that an unclaimed disclosed feature is essential to any claim. Rather, inventive subject matter may lie in less than all features of a particular disclosed embodiment. Thus, the following claims are hereby incorporated into the Detailed Description as examples or embodiments, with each claim standing on its own as a separate embodiment, and it is contemplated that such embodiments can be combined with each other in various combinations or permutations. The scope of the invention should be determined with reference to the appended claims, along with the full scope of equivalents to which such claims are entitled.

The invention claimed is:

1. A method of preparing a surgical plan, the method comprising:
    video capturing a range of motion of an anatomic joint of a patient to obtain a range of motion video while the patient is wearing a body suit having markers located at multiple joints of the patient;
    x-ray imaging the patient in a pose while the patient is wearing the body suit having the markers and while the patient is adjacent a first scale marker placed into a field of view of a first x-ray imaging machine to obtain directional medical images showing the markers relative to bones of the patient;
    registering the medical images to templating x-ray images of a skeleton of the patient including a second scale marker in the templating x-ray images, the templating x-ray images being derived independently and directly from the patient separately from the medical images by x-ray imaging the patient with a second x-ray imaging machine while the second scale marker is in a field of view of the second x-ray imaging machine;

identifying potential impingement and stability issues in the anatomic joint based on correlated images of the range of motion video and the medical images by comparing locations of the markers in the range of motion video and the medical images;

sizing and positioning a prosthetic implant on the templating x-ray images using the identified potential impingement and stability issues of the anatomic joint through the registered medical images to obtain position and orientation data;

electronically saving the position and orientation data of the prosthetic implant in a computer readable storage medium, the electronically saved position and orientation data being configured for use with a surgical navigation system in a format that allows the surgical navigation system to guide positioning of the prosthetic implant within a coordinate system maintained by the surgical navigation system during a surgical procedure; and configuring an instrument based on the position and orientation data.

2. The method of claim 1, wherein the potential impingement and stability issues in the anatomic joint are determined relative to a neighboring joint sharing a bone with the anatomic joint for a patient-specific activity.

3. The method of claim 1, further comprising calibrating the range of motion video to the medical images by comparing locations of the markers in the range of motion video to locations of the markers in the x-ray imaging to generate a virtual representation of the x-rayed bones performing the range of motion.

4. The method of claim 2, wherein the medical procedure comprises a total hip arthroplasty such that the anatomic joint comprises a hip joint and the neighboring joint comprises a knee joint.

5. The method of claim 1, further comprising:
video capturing the range of motion of the anatomic joint of the patient and x-ray imaging the patient to obtain medical images at a non-sterile outpatient center; and registering the medical images to templating x-ray images of a skeleton of the patient in an operating room using a surgical system having a positioning system, wherein the outpatient center and the operating room are located separately from each other at different facilities at different locations.

6. The method of claim 1, wherein registering the medical images to templating x-ray images of the skeleton of the patient comprises comparing a size of the anatomic joint in the medical images to a size of the anatomical joint in the templating x-ray images using the first and second scale markers.

7. The method of claim 6, wherein comparing a size of the anatomic joint in the medical images to a size of the anatomic joint in the templating x-ray images comprises comparing scaling information of the medical images obtained from the first scale marker with scaling information of the templating x-ray images obtained from the second scale marker such that sizing information of the anatomic joint can be transferred between the medical images and the templating x-ray images.

8. The method of claim 1, further comprising:
determining the scale of the medical x-ray images using the first scale marker;

templating the size and location of hypothetical implants on the medical x-ray images from the scale of the medical x-ray images; and determining the size of the prosthetic implant for implanting into the patient using a scaling factor determined from the second scale marker in the templating images.

* * * * *